United States Patent [19]
McGill, III et al.

[11] Patent Number: 6,025,495
[45] Date of Patent: Feb. 15, 2000

[54] REGIOSELECTIVE ALKYLATION PROCESS FOR PREPARING SUBSTITUTED BENZO[B]THIOPHENES

[75] Inventors: John McNeill McGill, III, Lafayette; Randal Scott Miller, Carmel, both of Ind.

[73] Assignee: Eli Lilly and Company, Indianapolis, Ind.

[21] Appl. No.: 09/069,276

[22] Filed: Apr. 29, 1998

Related U.S. Application Data

[60] Provisional application No. 60/045,132, Apr. 30, 1997.

[51] Int. Cl.[7] .................. C07D 409/10; C07D 413/10; C07D 333/52
[52] U.S. Cl. ................... 546/202; 540/596; 544/145; 548/525; 549/51
[58] Field of Search ............... 549/51; 548/525; 546/202; 544/145; 540/596

[56] References Cited

U.S. PATENT DOCUMENTS

| | | | |
|---|---|---|---|
| 3,394,125 | 7/1968 | Crenshaw | 260/326.5 |
| 3,413,305 | 11/1968 | Crenshaw | 260/326.5 |
| 4,133,814 | 1/1979 | Jones et al. | 260/326 |
| 4,358,593 | 11/1982 | Jones et al. | 546/202 |
| 4,380,635 | 4/1983 | Peters | 546/202 |
| 4,418,068 | 11/1983 | Jones et al. | 424/267 |
| 5,223,510 | 6/1993 | Gubin et al. | 514/299 |
| 5,395,842 | 3/1995 | Labrie et al. | 514/320 |
| 5,470,854 | 11/1995 | Angerer et al. | 514/233 |
| 5,472,962 | 12/1995 | Sagamihara et al. | 514/233.5 |
| 5,482,949 | 1/1996 | Black et al. | 514/324 |
| 5,552,412 | 9/1996 | Cameron et al. | 514/317 |
| 5,629,425 | 5/1997 | Labell et al. | 546/202 |

FOREIGN PATENT DOCUMENTS

| | | |
|---|---|---|
| 0062503 | 10/1982 | European Pat. Off. . |
| 0062504 | 10/1982 | European Pat. Off. . |
| 0 605 193 | 7/1994 | European Pat. Off. . |
| 2097392 | 4/1982 | United Kingdom . |
| 2096608 | 10/1982 | United Kingdom . |
| 2097788 | 11/1982 | United Kingdom . |
| WO93/10741 | 6/1993 | WIPO . |
| WO95/10513 | 4/1995 | WIPO . |

OTHER PUBLICATIONS

Jones, C.D., et al, *J. Med. Chem.* 27(8) 1057–1066 (1984).
Romeo Wagner, *Synthetic Organic Chemistry*, (171–172) 1953.
Jones, C.D., et al *J. Med. Chem.* 35(5) 931–938 (1992).
Kym, R.P. et al, *J. Med. Chem.*, 36 (24), 3911–3921 (1993).
Jackson, T.G., et al *J. Chem. Soc.* 1728–1729 (1969).
Kametani, et al *J. Org. Chem.* 41 (15) 2545–2547 (1976).
Crenshaw, R.R., et al *J. Med. Chem.* 14(12) 1185–1190 (1971).

*Primary Examiner*—Mukund J. Shah
*Assistant Examiner*—Brenda Coleman
*Attorney, Agent, or Firm*—Gilbert T. Voy

[57] ABSTRACT

The present invention provides processes for the regioselective alkylation of benzothiophenes.

6 Claims, No Drawings

REGIOSELECTIVE ALKYLATION PROCESS FOR PREPARING SUBSTITUTED BENZO[B] THIOPHENES

This application claims the benefit of U.S. Provisional Application Ser. No. 60/045,132 filed Apr. 30, 1997.

TECHNICAL FIELD

The present invention relates to chemical processes. More particularly, the present invention relates to a regioselective alkylation process for preparing 2-(4-hydroxyphenyl)-3-[4-(W-substituted amino)alkoxybenzoyl]benzo[b]thiophene compounds.

BACKGROUND OF THE INVENTION

The compound 6-hydroxy-2-(4-hydroxyphenyl)-3-[4-(2-piperidinoethoxy)benzoyl]benzo[b]thiophene, known also by its generic chemical name, raloxifene, is an important member of the class of compounds known as selective estrogen receptor modulators(SERMs). That compound is disclosed in U.S. Pat. No. 4,418,068.

Some of the compounds prepared by the present processes, including raloxifene, were first described in U.S. Pat. No. 4,133,814. That patent taught the use of phenacyl, halophenacyl, and alkyl protecting groups for phenolic hydroxyl groups. Those alkyl protecting groups may be removed by treating the phenolic ethers with pyridine hydrochloride.

The process described in U.S. Pat. No. 4,358,593 used additional protecting groups (for example, acetyl, substituted acetyl, benzoyl, alkylsulfonyl, and arylsulfonyl groups) for preparing 6-hydroxy-2-(4-hydroxyphenyl)-3-[4-(2-aminoethoxy)benzoyl]-benzo[b]thiophenes. That patent further taught the use of classical Friedel-Crafts catalysts in the acylation of the protected 2-(4-hydroxyphenyl)-6-hydroxybenzo[b]thiophene, including metal halides such as aluminum chloride, aluminum bromide, zinc chloride, boron trifluoride, boron tribromide, titanium tetrachloride, titanium tetrabromide, stannic chloride, stannic bromide, bismuth trichloride, and ferric chloride. Subsequent to acylation, the protecting group was generally removed under basic conditions.

The process described in U.S. Pat. No. 5,470,854 taught the use of methyl protecting groups that could be cleaved in a one pot process during the Friedel-Crafts acylation by particular acylation catalysts. That patent taught that boron halides, such as boron trichloride and boron tribromide, were particularly useful in the Friedel-Crafts acylation, and for the cleavage of arylmethyl ethers.

SUMMARY OF THE INVENTION

The present invention provides a process for preparing compounds of formula VI

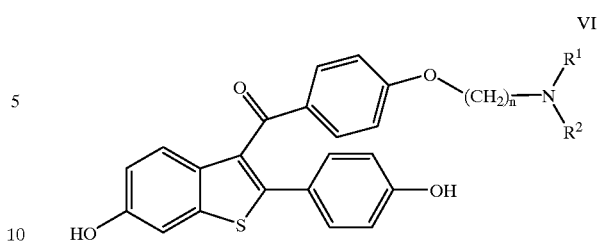

wherein $R^1$ and $R^2$ each are independently $C_1$–$C_4$ alkyl, or combine to form, together with the nitrogen to which they are attached, a piperidinyl, pyrrolidinyl, methylpyrrolidinyl, dimethylpyrrolidinyl, morpholino, dimethylamino, diethylamino, or 1-hexamethyleneimino ring, and n is 2 or 3, which includes the reaction of a compound of formula IV

IV

[structure]

with a compound of formula V

V

Y—(CH₂)ₙ—N⟨R¹,R²⟩ wherein Y is chloro or 4-methylphenylsulfonyl-O-, and $R^1$ and $R^2$ and n are as defined above, in the presence of a suitable base.

DETAILED DESCRIPTION OF THE INVENTION

General terms used in the description of chemical formula herein bear their usual meanings. For example, the term "$C_1$–$C_4$ alkyl" refers to straight or branched chains of 1 to 4 carbon atoms including, methyl, ethyl, propyl, isopropyl, butyl, n-butyl, and isobutyl; and the term "alkyl" encompasses the groups included in the definition of "$C_1$–$C_4$ alkyl" in addition to groups such as pentyl, isopentyl, hexyl, isohexyl, and the like. The term "halo" includes bromo, chloro, fluoro, and iodo. The term "lower alcohols" refers to $C_1$–$C_4$ alcohols including methanol, ethanol, propanol, isopropanol, butanol, n-butanol, isobutanol, and the like. The abbreviation "Tos" refers to a 4-methylphenylsulfonyl group.

The term chlorinating reagents encompasses such reagents as thionyl chloride, molecular chlorine, N-chlorosuccinimide, benzeneseleninylchloride/aluminum chloride, and the like.

The term "hydroxy protecting group" denotes a group understood by one skilled in the organic chemical arts of the type described in Chapter 2 of "protective Groups in Organic Synthesis, 2nd Edition, T. H. Greene, et al., John Wiley & Sons, New York, 1991. Such groups include, for example, ether groups, including methyl and substituted methyl ether groups such as methyl ether, methoxymethyl ether, methylthiomethyl ether, tert-buylthiomethyl ether, (phenyldimethylsilyl)methoxymethyl ether, benzyloxymethyl ether, p-methoxy-benzyloxymethyl ether, and tert-butoxy-methyl ether; substituted ethyl ether groups such as ethoxyethyl ether, 1-(2-chloroethoxy)ethyl ether, 2,2,2-trichloroethoxymethyl ether, and 2-(trimethylsilyl)ethyl ether; phenyl and substituted phenyl ether groups such as phenyl ether, p-chlorophenyl ether, p-methoxyphenyl ether, and 2,4-dinitrophenyl ether; benzyl and substituted benzyl ether groups such as benzyl ether, p-methoxybenzyl ether, o-nitrobenzyl ether, and 2,6-dichlorobenzyl ether; and alkyl-silyl ether groups such as trimethyl- triethyl- and triisopropylsilyl ethers, mixed alkylsilyl ether groups such as dimethylisopropylsilyl ether, and diethylisopropylsilyl ether; and ester protecting groups such as formate ester, benzylformate ester, mono- di- and trichloroacetate esters, phenoxyacetate ester, and p-chlorophenoxyacetate and the like. Preferred protecting groups encompassed in this invention are methyl groups, for example wherein R is methyl.

Methods for protecting hydroxy groups with one of the groups listed above, or as provided in the text by Greene, et al., as well as methods for cleaving or removing the protecting groups, are discussed in the text and the references cited therein and, are well known to one skilled in the art.

num chloride, boron trifluoride, boron trichloride, boron tribromide, titanium tetrachloride, titanium tetrabromide, stannic chloride, stannic bromide, bismuth trichloride, and ferric chloride.

A reaction which is run "neat" is a reaction where one of the reagents also serves as a solvent.

The term "kinetic base" refers to a base which provides a non-reversible deprotonation of an acidic substrate, such as alkyl metals (such as butyl lithium or ethyl magnesium bromide), metal amides (such as lithium diisopropyl amide), or a metal hydride (such as sodium hydride, lithium hydride).

The overall process of the present invention, including the preparation of starting materials, is depicted in Scheme 1 wherein R is independently at each occurrence a hydroxy protecting group, X is an acyl activating group, and n, $R^1$, $R^2$, and Y are as described, supra.

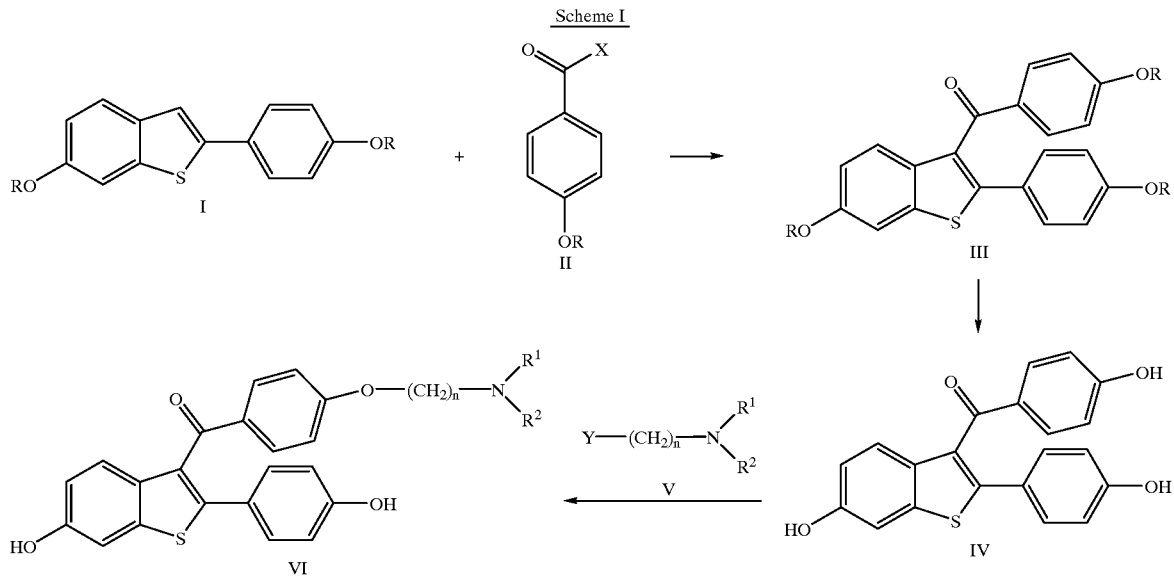

Scheme I

The term "acyl activating group" refers to a substituent to a carbonyl that promotes nucleophilic addition reactions to the carbonyl. Suitable activating substituents are those which have a net electron withdrawing effect on the carbonyl. Typical electron withdrawing groups include groups that when combined with the carbonyl form an ester or amide. Such groups include hydroxybenzotriazole, imidazole, nitrophenol, pentachlorophenol, N-hydroxysuccinimide, dicyclohexylcarbodiimide, N-hydroxy-N-methoxyamine, and the like. The term acyl activating group also encompasses groups that when combined with the carbonyl form an acid anhydride. Such groups include small carboxylic acids such as acetic, formic, sulfonic, methanesulfonic, ethanesulfonic, benzenesulfonic, or p-tolylsulfonic acid, and the like. Furthermore, a halogen attached to a carbonyl activates it for nucleophilic addition. Suitable halogens include chloro, bromo, or iodo.

By the term "Lewis acid catalyst" is meant catalysts including metal halides, such as aluminum bromide, alumi- A compound of formula I may be acylated with a compound of formula II. For example, a compound of formula I may be dissolved in a suitable solvent in the presence of Lewis acid catalyst and a compound of formula II added. Suitable solvents include chlorinated alkane solvents, such as chloroform, 1,2-dichloroethane, 1,2,3-trichloropropane, aromatic solvents such as benzene and chlorobenzene, hydrocarbon solvents such as petroleum ether, hexane, mixtures thereof, and the like. Methylene chloride is typically the preferred solvent. Suitable Lewis acid catalysts are of the type described, supra, or in Olah, "Friedel-Crafts and Related Reactions," Interscience Publishing Co., New York, 1963. Aluminum chloride or boron trichloride is the preferred Lewis acid catalyst. The Lewis acid catalyst is typically employed in a substantial molar excess. For example, a 1.5 to 2.5 molar excess, relative to the compound of formula I, is generally employed. A 2.0 molar excess is preferred. The compound of formula II is typically employed in a slight molar excess. For example, a 1.01 to 1.25 molar excess, relative to the compound of formula I is generally employed. A 1.1 molar excess is preferred. The reaction is preferably carried out at about room temperature for about 1 hour.

When boron trichloride or boron tribromide is the Lewis acid catalyst employed, the hydroxy protecting group at the 3 position of the benzothiophene ring in compounds of formula III is not removed in the acylation step. The removal of the hydroxy protecting groups at the 2 and 6 positions is not important in the overall process because in the next step all of the protecting groups are deliberately removed.

A compound of formula IV may be obtained by treating a compound of formula III in a suitable solvent with pyridinium hydrochloride. Generally, and preferably, the reaction is run neat in pyridinium hydrochloride. The pyridinium hydrochloride is typically employed in a substantial molar excess. For example, a 15 to 30 molar excess, relative to the compound of formula III is generally employed. A 20 molar excess is preferred. The reaction is preferably carried out at about 185° C. for about 1.5 hours.

A compound of formula VI may be obtained by the dissolution or suspension of a compound of formula IV in a suitable polar solvent in the presence of a suitable base followed by the addition of a compound of formula V. Suitable solvents include dimethylformamide, lower alcohols, 1,3-dimethyl-2-imidazolidinone, mixtures thereof, and the like. Dimethylsulfoxide is the preferred solvent. Suitable bases include non-kinetic bases such as carbonates, bicarbonates, or hydroxides, (for example, sodium hydroxide, potassium bicarbonate, or sodium hydroxide) and kinetic bases such as alkyl lithiums (for example, n-butyl lithium) or sodium hydride. A kinetic base, specifically sodium hydride, is the preferred base. The base is typically employed in a slight molar excess. For example, a 1.01 to 1.15 molar excess, relative to the compound of formula IV, is generally employed. A 1.05 molar excess is preferred. A compound of formula V is typically employed in a slight molar excess. For example, a 1.01 to 1.15 molar excess, relative to the compound of formula IV is generally employed. A 1.05 molar excess is preferred. The reaction is preferably carried out at about 35° C. for about 2 hours after addition of the base and then at about 65° C. for about 16 hours after the addition of a compound of formula V.

Surprisingly, when the alkylation is performed as described in this invention, the alkylation proceeds in a regioselective fashion to give a compound of formula VI.

Compounds of formula I are known in the art and are prepared, for example, as described by Peters in U.S. Pat. No. 4,380,635, or Jones, et al., in U.S. Pat. Nos. 4,133,814 and 4,418,068. Compounds of formula II are known in the art and are generally commercially available or prepared by methods well known in the art from readily available starting materials.

Compounds of formula V are commercially available or may be prepared from commercially available compounds of formula VII as shown in Scheme 2 wherein n, $R^1$, and $R^2$ are as defined, supra.

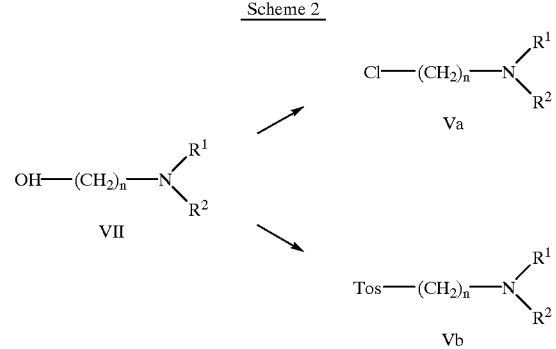

Scheme 2

Compounds of formula V include compounds of both formula Va and compounds of formula Vb as illustrated above. For example, compounds of formula V where Y is chloro may be prepared from compounds of formula VII by dissolving a compound of formula VII in a suitable solvent and adding thionyl chloride or 2,2,2-trifluoroethylsulfonyl chloride. Similarly, compounds of formula V where Y is 4-methylphenylsulfonyl-O- may be prepared from compounds of formula VII by the addition of 4-methylphenylsulfonyl chloride. Suitable solvents include acetonitrile, chloroform, ethyl acetate, dimethylformamide, tetrahydrofuran, lower alcohols, and the like. A preferred solvent is methylene chloride. The additive is typically employed in a slight molar excess. For example, a 1.01 to 1.3 molar excess, relative to a compound of formula VII, is generally employed. A 1.12 molar excess is typically preferred. The reaction is typically and preferably carried out at about 0° C. during the addition and then at about room temperature for about 12 hours. A preferred embodiment of this invention employs 2-chloroethylpiperidine (a compound of formula V wherein n is 2, $R^1$ and $R^2$ combine to form piperidinyl, and Y is chloro) generated and used in situ from 2-hydroxyethylpiperidine (a compound of formula VII where n is 2 and $R^1$ and $R^2$ combine to form piperidinyl) by the process described in Scheme 2, in the overall process of the invention described in Scheme 1.

In general, the reactions of Schemes 1 and 2 are substantially complete in about 15 minutes to 72 hours when conducted at a temperature range of from about 0° C. to the reflux temperature of the reaction mixture. The reaction solvent choices are not critical so long as the solvent employed is inert to the ongoing reaction and the reactants are sufficiently solubilized to effect the desired reaction. Once a reaction is complete, the intermediate compound may be isolated, if desired, by procedures known in the art. For example, the compound may be crystallized and then collected by filtration, or the reaction solvent may be removed by extraction, evaporation, or decantation. The intermediate may be further purified, if desired by common techniques such as recrystallization or chromatography over solid supports such as silica gel or alumina. The compounds of formula I are preferably isolated before use in subsequent reactions.

The optimal time for performing the reactions of the invention can be determined by monitoring the progress of the reaction via conventional chromatographic techniques. Furthermore, it is preferred to conduct the reactions of the invention under an inert atmosphere, such as, for example, argon or nitrogen.

The following examples are provided for the purpose of illustrating the present invention and are not intended to be limiting upon the scope of the invention.

EXAMPLES

Preparation 1

2-(4-Methoxyphenyl)-3-(4-Methoxybenzoyl)-6-Methoxybenzo[b]thiophene

A 250 mL, 3 neck, round bottomed flask fitted with a mechanical agitator and connected to a sodium hydroxide scrubber is purged with nitrogen and charged with 2-(4-methoxyphenyl)-6-methoxybenzo[b]thiophene (5.3 g, 19.6 mmol), p-anisoyl chloride (3.68 g, 21.56 mmol), and 100 mL of methylene chloride. To this slurry at 20° C. is added boron trichloride (3.4 mL, 39.8 mmol) which had been condensed in a graduated cylinder. The reaction mixture is quenched after 40 minutes by the slow addition of 50 mL of methanol over approximately 5 minutes followed by addition of 50 mL of water over 5 minutes. The organic phase is washed with 50 mL brine, dried over sodium sulfate, filtered, and concentrated affording a dark orange oil. Addition of 10 mL of methanol followed by sonication for 5 minutes resulted in crystallization of 7.1 g of crude product as a yellow solid. The crude material is recrystallized from 3:1 hexanes/toluene affording 5.9 g of product as pale yellow crystals. (75%).

mp 118–119° C.; $^1$H NMR (300.1 MHz, DMSO-d6) δ 3.66 (s, 3H), 3.77 (s, 3H), 3.86 (s, 3H), 6.84 (d, 2H), 6.88 (d, 2H), 6.98 (dd, 1H), 7.32 (d, 2H), 7.34 (s, 1H), 7.63 (d, 1H), 7.68 (d, 2H); $^{13}$C NMR (75.5 MHz, DMSO-d6) d 55.2, 55.5, 105.2, 114.1, 114.4, 115.0, 123.3, 125.2, 129.6, 129.7, 130.2, 131.8, 133.2, 139.4, 140.8, 157.4, 159.5, 163.6, 192.4; MS (FD+) m/e 405 (30), 404 (100); Analysis calc'd for $C_{24}H_{20}O_4S$: C, 71.27; H, 4.98; S, 7.93; found: C, 71.51; H, 4.99; S, 7.98.

Preparation 2

2-(4-Hydroxyphenyl)-3-(4-Methoxybenzoyl)-6-Hydroxybenzo[b]thiophene

A 100 mL, 3 neck, round bottom flask fitted with a mechanical agitator, glass stopper, and outlet to a caustic scrubber is charged with p-anisoyl chloride (3.47 g, 20.34 mmol), 2-(4-methoxyphenyl)-3-(4-methoxybenzoyl)-6-methoxybenzo[b]thiophene (5.0 g, 18.49 mmol) and 30 mL 1,2-dichloroethane. The mixture is cooled to 0–5° C. and previously condensed boron trichloride (4.7 mL, 55.0 mmol) is added in one portion. The mixture is stirred at 0–50° C. for 7.5 hours then more boron trichloride (4.7 mL, 55.0 mmol) is added. The cooling bath is removed and the reaction mixture is stirred at ambient temperature for 16 hours. After the overnight stir, the mixture is poured into 500 mL of agitated ice/water which caused precipitation of the monomethoxy product. The reaction vessel is rinsed in with 1,2-dichloroethane and the slurry is stirred for 1 hour. Then, 200 mL of methylene chloride is added and the mixture is vacuum filtered washing with methylene chloride. The solid is dried overnight in a vacuum oven at 40° C. to afford 6.3 g (82.4%) of monomethoxy product as a yellow solid. An analytical sample is obtained by chromatography on silica gel (20:1 methylene chloride/methanol). mp 127–128° C. (dec); $^1$H NMR (300.1 MHz, DMSO-d6) δ 3.76 (s, 3H), 6.66 (d, 2H), 6.85 (dd, 1H), 6.87 (d, 2H), 7.16 (d, 2H), 7.25 (d, 1H), 7.33 (s, 1H), 7.66 (d, 2H), 9.76 (br s, 2H); 13C NMR (75.5 MHz, DMSO-d6) d 55.5, 107.1, 114.0, 115.2, 115.7, 123.3, 123.8, 129.7, 131.8, 132.3, 139.2, 140.4, 155.4, 157.8, 163.5, 192.6; MS (FD+) m/e 376(100), 377(25), 378(7); Analysis calc'd for $C_{22}H_{16}O_4S$: C, 70.20; H, 4.28; S, 8.52; found: C, 70.09; H, 4.27; S, 8.45.

Preparation 3

2-Chloroethylpiperidine

Into a 50 mL round bottom flask is placed 6.40 g (33.6 mmol) of p-toluenesulfonyl chloride and 25 mL of methylene chloride. The resulting solution is cooled with an ice bath as 4.00 g (31.0 mmol) of 1-piperidinoethanol in 6 mL of methylene chloride is added dropwise. After the addition is complete, the ice bath is removed and the resulting slurry is stirred for about 12 hours. The reaction mixture is concentrated on a rotary evaporator to yield a solid residue which may then be used as in Preparation 4 below.

Preparation 4

2-(4-Hydroxyphenyl)-3-(4-Hydroxybenzoyl)-6-Hydroxybenzo[b]thiophene

A 250 mL, 3 neck, flask fitted with a thermometer, condenser, and stopper is charged 2-(4-hydroxyphenyl)-3-(4-methoxybenzoyl)-6-hydroxybenzo[b]thiophene (3.0 g, 7.97 mmol) and pyridine hydrochloride (18.5 g, 160 mmol). The contents are heated to 185–190° C. and held at this temperature for 90 minutes. The hot mixture is then poured into 250 mL of ice/water. A yellow solid formed with this addition. The material is extracted into 250 mL of ethyl acetate. The aqueous is then back-extracted with 100 mL of ethyl acetate. The combined organics are washed with 150 mL 1N hydrochloric acid and 150 mL brine. The solvent is removed in vacuo giving a viscous oil. To the oil is added 10 mL of 1:1 methylene chloride/hexanes which induced crystallization. The slurry is cooled to 0° C. and stirred at this temperature for 1 hour. The product is collected by vacuum filtration and washed with 25 mL of 4:1 hexanes/methylene chloride. Drying the solid at 100° C. for 5 hours afforded 2.5 g (86.2%) of a dark yellow solid containing approximately 3% monomethoxy starting material. An analytical sample is obtained by chromatography on silica gel (15:1 methylene chloride:methanol). mp 135° C. (dec); $^1$H NMR (300.1 MHz, DMSO-d6) δ 6.67 (d, 2H), 6.71 (d, 2H), 6.85 (dd, 1H), 7.17 (d, 2H), 7.25 (d, 1H), 7.32 (d, 1H), 7.57 (d, 2H), 9.73 (br s, 2H), 10.41 (br s, 1H); $^{13}$C NMR (75.5 MHz, DMSO-d6) d 107.1, 115.1, 115.4, 115.6, 123.4, 123.9, 128.4, 129.7, 129.9, 132.1, 132.4, 139.2, 140.0, 155.4, 157.8, 162.5, 192.4; MS (FD+) m/e 362 (100), 363 (24), 364 (7); HRMS m/e calc'd for $C_2H_{15}O_4S$ (M+1): 363.069106, found 363.06990.

Example 1

[6-Hydroxy-2-(4-Hydroxyphenyl)-3-[4-(2-Piperidinoethoxy)benzyl]benzo[b]thiophene Hydrochloride]

A 50 mL, 3 neck, round bottomed flask fitted with a mechanical agitator, nitrogen purging inlet, and thermometer is charged with 2-(4-hydroxyphenyl)-3-(4-hydroxybenzoyl)-6-hydroxybenzo[b]thiophene (1.0 g, 2.76 mmol) and 25 mL dimethylsulfoxide. The solution is then charged with sodium hydride (60% oil dispersion, 116 mg, 2.90 mmol) in one portion. A large amount of gas evolution is noted with this addition. The temperature of the mixture is adjusted to 35° C. and the reaction allowed to stir at this temperature for 2 hours. 2-chloroethylpiperidine (428 mg, 2.90 mmol) is then added via syringe in one portion. The 2-chloroethylpiperidine is rinsed with 0.3 mL dimethylsulfoxide. The reaction mixture is then warmed to 65° C. and stirred for 16 hours. The mixture is then quenched by the slow addition of 25 mL deionized water. The contents are transferred to a 250 mL Erlenmeyer flask and another 50 mL deionized water is added. After stirring vigorously for 1 hour, the solid is collected by vacuum filtration and washed with water. After drying, 1.3 g of a mixture of 6-hydroxy-2-(4-hydroxyphenyl)-3-[4-(2-piperidinoethoxy)benzyl]benzo[b]thiophene and trihydroxy starting material is obtained. Purification by flash chromatography (methanol) afforded 550 mg of a viscous yellow oil which is crystallized from 20:1 methanol/water at pH 1 giving 370 mg of a light yellow powder. mp 252–256° C. (Lit. 258° C.); $^1$H NMR (300.1 MHz, DMSO-d6) δ 1.32 (m, 1H), 1.65 (m, 1H), 1.73 (br s, 4H), 2.93 (m, 2H), 3.40 (m, 4H), 3.62 (br s, 1H), 4.45 (m, 2H), 6.68 (d, 2H), 6.83 (dd, 1H), 6.94 (d, 2H), 7.13 (d, 2H), 7.24 (d, 1H), 7.37 (d, 1H), 7.58 (d, 2H), 9.88 (br s, 1H), 10.46 (br s, 1H); $^{13}$C NMR (75.5 MHz, DMSO-d6) d 23.9, 25.5, 25.6, 54.3, 54.4, 57.1, 65.9, 107.1, 114.5, 115.2, 115.7, 123.3, 123.6, 129.63, 129.64, 129.7, 131.8, 132.2, 139.2, 140.3, 155.6, 158.0, 162.8, 192.6; MS (FAB+) m/e 474 (91), 155 (70), 152 (97), 135 (99), 119 (100); Analysis calc'd for $C_{28}H_{28}NO_4SCl$: C, 65.99; H, 5.54; N, 2.75; Cl, 6.87; S, 6.28; found: C, 64.78; H, 5.49; N, 2.86; Cl, 7.04; S, 6.33.

We claim:

1. A process for preparing a compound of formula VI

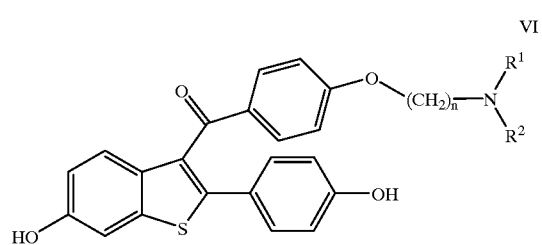

VI wherein:

$R^1$ and $R^2$ each are independently $C_1$–$C_4$ alkyl, or combine to form, together with the nitrogen atom to which they are attached, a piperidinyl, pyrrolidinyl, methylpyrrolidinyl, dimethylpyrrolidinyl, morpholino, or 1-hexamethyleneimino ring; and n is 2 or 3;

or a pharmaceutically acceptable salt or solvate thereof, which comprises:

reacting a compound of formula IV

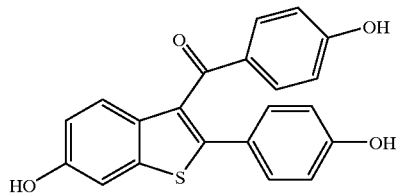

IV with a compound of formula V

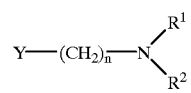

V wherein Y is chloro or 4-methylphenylsulfonyl-O-, and n, $R^1$, and $R^2$ are as defined above;

in the presence of a suitable base.

2. A process according to claim 1 wherein said suitable base is sodium hydride.

3. A process according to claim 1 wherein said compound of formula V is generated from the reaction of a chlorinating reagent and a compound of formula VII

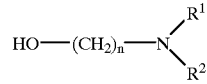

VII and the resulting compound of formula V is employed in situ.

4. A process according to claim 3 wherein said chlorinating reagent is thionyl chloride.

5. A process according to claim 1 wherein n is 2 and $R^1$ and $R^2$ combine to form, together with the nitrogen to which they are attached, a piperidinyl ring.

6. A process according to claim 1 wherein Y is chloro.

* * * * *